United States Patent
Jiang et al.

(10) Patent No.: US 10,751,061 B2
(45) Date of Patent: Aug. 25, 2020

(54) PUSHING APPARATUS AND DELIVERY SYSTEM

(71) Applicant: LIFETECH SCIENTIFIC (SHENZHEN) CO., LTD, Shenzhen (CN)

(72) Inventors: Wei Jiang, Shenzhen (CN); Gang Wang, Shenzhen (CN); Renmei Ma, Shenzhen (CN)

(73) Assignee: LIFETECH SCIENTIFIC (SHENZHEN) CO., LTD, Shenzhen (CN)

( * ) Notice: Subject to any disclaimer, the term of this patent is extended or adjusted under 35 U.S.C. 154(b) by 242 days.

(21) Appl. No.: 15/777,317

(22) PCT Filed: Apr. 29, 2016

(86) PCT No.: PCT/CN2016/080685
§ 371 (c)(1),
(2) Date: May 18, 2018

(87) PCT Pub. No.: WO2017/113554
PCT Pub. Date: Jul. 6, 2017

(65) Prior Publication Data
US 2018/0296221 A1 Oct. 18, 2018

(51) Int. Cl.
*A61B 17/12* (2006.01)
*A61M 39/06* (2006.01)
*A61B 17/00* (2006.01)

(52) U.S. Cl.
CPC .. *A61B 17/12031* (2013.01); *A61B 17/12022* (2013.01); *A61M 39/06* (2013.01);
(Continued)

(58) Field of Classification Search
CPC .......... A61F 2/95; A61M 39/06; A61B 17/12; A61B 17/12022; A61B 17/12031;
(Continued)

(56) References Cited

U.S. PATENT DOCUMENTS 5,626,136 A * 5/1997 Webster, Jr. ......... A61B 5/0422
600/373
5,643,277 A 7/1997 Soehendra et al.
(Continued)

FOREIGN PATENT DOCUMENTS

CN 101416890 A 4/2009
CN 102665608 A 9/2012
(Continued)

OTHER PUBLICATIONS

International Search Report dated Oct. 12, 2016 of corresponding International Application No. PCT/CN2016/080685; 9 pgs.
(Continued)

*Primary Examiner* — George J Ulsh
(74) *Attorney, Agent, or Firm* — Maier & Maier, PLLC

(57) ABSTRACT

A pushing apparatus and conveying system for an interventional medical instrument. By covering a thermoplastic elastomer on the surface of a steel cable to form an overlay film, steel cable support is improved when guaranteeing the flexibility thereof so that it is difficult for the instrument to deviate from a predetermined position when conveying the instrument, the operation time is shortened, and the operation risk of patients is reduced. Meanwhile, in the conveying system, a sealing member is provided in an inner cavity of
(Continued)

a hemostasis valve body to match the overlay film of the steel cable so that the distal end of the hemostasis valve body is isolated from the outside, and the release effect of the instrument can be assessed by radiography before the instrument is released from the steel cable in operation, thereby effectively reducing harm to patients.

15 Claims, 5 Drawing Sheets

(52) U.S. Cl.
CPC ............... *A61B 17/12122* (2013.01); *A61B 2017/00862* (2013.01); *A61B 2017/00955* (2013.01); *A61B 2017/12004* (2013.01); *A61B 2017/1205* (2013.01)

(58) Field of Classification Search
CPC .......... A61B 2017/00862; A61B 2017/00955; A61B 2017/12004; A61B 2017/1205; A61B 17/12122
See application file for complete search history.

(56) References Cited

U.S. PATENT DOCUMENTS

| | | | |
|---|---|---|---|
| 6,571,131 B1* | 5/2003 | Nguyen | A61B 18/1492 607/122 |
| 2008/0312597 A1* | 12/2008 | Uihlein | A61M 25/09 604/164.13 |
| 2013/0110223 A1 | 5/2013 | Munsinger et al. | |
| 2014/0324096 A1* | 10/2014 | Ngo | A61B 17/12022 606/200 |
| 2017/0197059 A1* | 7/2017 | Toyota | A61M 25/0045 |

FOREIGN PATENT DOCUMENTS

| | | |
|---|---|---|
| CN | 202859386 U | 4/2013 |
| CN | 103987325 A | 8/2014 |
| CN | 104586440 A | 5/2015 |

OTHER PUBLICATIONS

Office Action dated Feb. 27, 2020, in corresponding Indian Application No. 201817020672; 6 pages.

* cited by examiner

B -B

PUSHING APPARATUS AND DELIVERY SYSTEM

FIELD

The present application relates to the technical field of interventional medical instruments, and relates to a pushing apparatus for pushing the interventional medical instruments and a manufacturing method there of, as well as a delivery system of the interventional medical instruments.

BACKGROUND

Treating cardiovascular diseases by catheter intervention is a conventional therapy at the present, and it specifically means that various materials, devices and the like are put into parts such as the heart, an artery blood vessel and a vein of a human body via a catheter intervention therapy to treat the cardiovascular diseases.

For example, an interventional medical instrument, such as an Atrial Septal Defect (ASD) occluder, a Ventricular Septal Defect (VSD) occluder, a Patent Ductus Arteriosus (PDA) occluder and a Patent Foramen Ovale (PFO) occluder, is placed via the catheter intervention method, and then reaches a defective part of the heart so as to occlude the defect to treat congenital heart diseases. For another example, an occluder may be put into a left atrial appendage through a catheter intervention method to prevent a left atrial appendage thrombus caused by atrial fibrillation and avoid apoplexy caused by a fact that the thrombus goes up to a brain, or prevent systematic embolization caused by a fact that the thrombus reaches other portions of a body through a blood circulation system of a human body. Or for another example, a lung volume reduction device is delivered to a diseased position of a bronchus of the lung to treat pulmonary emphysema.

During delivery of the interventional medical device into the heart, the artery blood vessel, the vein, the left atrial appendage and the bronchus of the lung through a delivery system, the interventional medical device is generally pushed to a predetermined part through a flexible pushing steel cable, and then connection between the interventional medical device and the pushing steel cable is cut off to release the interventional medical device; and whether the release position of the interventional medical device is appropriate or not, whether the interventional medical device is poorly spread or not, and whether an operation effect is satisfactory or not are confirmed through radiography or ultrasonic.

In an actual use process, to reduce trauma of patients, it should reduce inner and outer diameters of a delivery sheath as much as possible. However, under a condition that the model of the selected interventional medical device is not changed, the inner diameter of the sheath used cooperatively is smaller, and the pushing resistance of the interventional medical device is greater; and particularly when a path of pushing the interventional medical device is relatively long, a supporting force of the flexible steel cable will be insufficient, which directly leads to a fact that it is relatively easy for the interventional medical device to deviate from a predetermined position, thus prolonging the operation time and increasing the operation risk of the patients.

SUMMARY

The pushing apparatus and the delivery system of the present application are applicable to delivery of an interventional device, such as a left atrial appendage occluder, for a defect part with a complicated anatomical structure.

The pushing apparatus and the delivery system of the present application are particularly applicable to delivery of an interventional device, such as a left atrial appendage occluder, for a defect part with a complicated anatomical structure.

The present application provides a pushing apparatus, including a steel cable. The steel cable includes a long-strip type steel cable main body, and also includes an overlay film arranged on the outer surface of the steel cable main body.

In one embodiment, the steel cable main body has a proximal end and a distal end which are opposite to each other. The proximal end of the overlay film is adjacent to the proximal end of the steel cable main body.

In one embodiment, the overlay film is made of a thermoplastic elastomer.

In one embodiment, the thermoplastic elastomer includes polyether block amide or thermoplastic polyurethane.

In one embodiment, the length of the overlay film along the longitudinal central axis of the steel cable main body is equal to or less than half of the length of the steel cable main body.

In one embodiment, the steel cable main body includes a long-strip type inner core which is formed by twisting at least three strands of steel wires, and the overlay film is arranged on the outer surface of the inner core.

In one embodiment, the steel cable main body also includes a steel wire arranged on the inner core, and the overlay film is arranged on the outer surface of the steel wire. The present application further provides a delivery system which includes the pushing apparatus.

The present application further provides a delivery system which includes a hemostasis apparatus. The hemostasis apparatus includes a hemostasis valve body having an inner cavity and a sealing member arranged in the inner cavity of the hemostasis valve body. A pore is formed in the sealing member. After the distal end of the steel cable main body penetrates through the hemostasis valve body from the distal end of the hemostasis valve body via the pore, the overlay film of the steel cable cooperates with the sealing member to isolate the distal end of the inner cavity of the hemostasis valve body from the outside world.

In one embodiment, the delivery system also includes a delivery sheath. The proximal end of the delivery sheath is connected with the distal end of the hemostasis apparatus, and an inner cavity of the delivery sheath is communicated with the inner cavity of the hemostasis apparatus.

The delivery sheath includes a main body portion and a shaping portion. The main body portion is connected between the hemostasis apparatus and the shaping portion.

The shaping portion includes a first shaping section; an included angle between the extending direction of the first shaping section and the extending direction of the main body portion ranges from 40 to 50 degrees; the extending direction of the first shaping section is a direction from the proximal end of the first shaping section to the distal end of the first shaping section; and the extending direction of the main body portion is a direction from the proximal end of the main body portion to the distal end of the main body portion.

In one embodiment, the shaping portion also includes a second shaping section. The first shaping section is connected between the main body portion and the second shaping section; an included angle between the extending direction of the second shaping section and a plane where the first shaping section and the main body portion are located ranges from 30 to 40 degrees; and the extending direction of the second shaping section is a direction from the proximal end of the second shaping section to the distal end of the second shaping section.

In one embodiment, the delivery system also includes an expansion tube; the outer diameter of the expansion tube is slightly less than the inner diameter of the delivery sheath; and the outer diameter of the head of the distal end of the expansion tube is gradually increased from the distal end to the proximal end.

In one embodiment, the expansion tube is provided with a shaping portion which is the same as the shaping portion of the delivery sheath in shape.

In one embodiment, the delivery system also includes a hollow loader connected between the delivery sheath and the hemostasis apparatus; and an inner cavity of the loader is communicated with the inner cavities of the delivery sheath and the hemostasis apparatus.

In one embodiment, the inner cavity of the hemostasis valve body has a conical section; the diameter of the proximal end of the conical section is greater than that of the distal end of the conical section; and the sealing member is adjacent to the proximal end of the conical section.

In one embodiment, the delivery system is used for delivering a left atrial appendage occluder; and the steel cable is detachably connected with the left atrial appendage occluder.

The present application further provides a manufacturing method of a pushing apparatus, including:

sleeving a steel cable main body with an overlap film tubular body; and melting the overlap film tubular body to integrate the overlap film tubular body with the steel cable main body.

In one embodiment, temperature for melting the overlap film tubular body ranges from 180 to 220 DEG C.

In one embodiment, after the step of sleeving the steel cable main body with the overlap film tubular body, and before the step of melting the overlap film tubular body, the manufacturing method also includes a step of sleeving the overlap film tubular body with a heat shrink tubing. The melting point of the heat shrink tubing is lower than that of the overlap film tubular body. After the step of melting the overlap film tubular body, the manufacturing method also includes a step of removing the heat shrink tubing.

In one embodiment, the overlap film tubular body is made of a thermoplastic elastomer.

In one embodiment, the thermoplastic elastomer includes polyether block amide or thermoplastic polyurethane.

Compared with the prior art, the present application has, at least, the advantages that the overlay film prepared from the thermoplastic elastomer is formed on the outer surface of the steel cable main body; the steel cable coated with the film may ensure that the distal end flexibly adapts to a bent blood vessel path, is higher in supporting property and pushing property, and is particularly suitable for a complicated vascular channel or treated part, such as left atrial appendage occlusion operation.

BRIEF DESCRIPTION OF THE DRAWINGS

FIG. 6b is a section view of 42 in a portion A in FIG. 6a;

FIG. 7 is a sectional view of the steel cable main body in FIG. 6a;

FIG. 8 is sectional views of the steel cable main body and the overlay film arranged on the outer surface of the steel cable main body in FIG. 6a;

FIGS. 9a-9d are schematic diagrams of a hemostasis apparatus of the delivery system in FIG. 1, which includes a hemostasis valve body having an inner cavity and a sealing member arranged in the inner cavity, wherein FIG. 9a is a front view; FIG. 9b is a section view of a portion B in FIG. 9a;

FIG. 9c is a section view of decomposition of the hemostasis valve body in FIG. 9a;

FIG. 9d is a local section view of the portion B in FIG. 9a after the sealing member deforms elastically;

DETAILED DESCRIPTION

For the purpose of making objectives, technical schemes and advantages of the present application clearer, a further detailed description will be made in conjunction with accompanying drawings and embodiments. It should be understood that the specific embodiments described herein are merely explanations of the present application, but not intended to limit the present application.

To make the description clear, the end close to an operator is regarded as a proximal end, and the end far away from the operator is regarded as a distal end.

Embodiment I

A delivery system 100 of Embodiment I is used for delivering an interventional medical device 200 to a diseased part and then releasing it. In this embodiment, the interventional medical device 200 is a left atrial appendage occluder. The delivery system 100 delivers the interventional medical device 200 to a left atrial appendage and then releases it; the interventional medical device 200 includes two occluding disks and a layer of occluding film arranged inside one occluding disk; and the occluding disks are made of a material having a shape memory function, so that during use, they may be stretched into lines. The occluding film is made of a polytetrafluoroethylene material with good biocompatibility.

Figure 1:
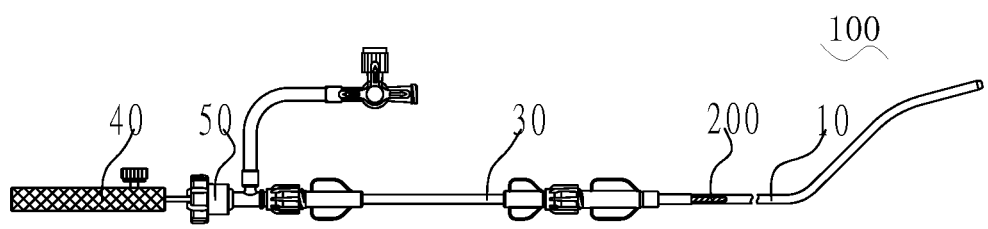
FIG. 1 is a schematic diagram of a delivery system of a first embodiment of the present application after the delivery system is loaded with an interventional medical device.
Figure 2:
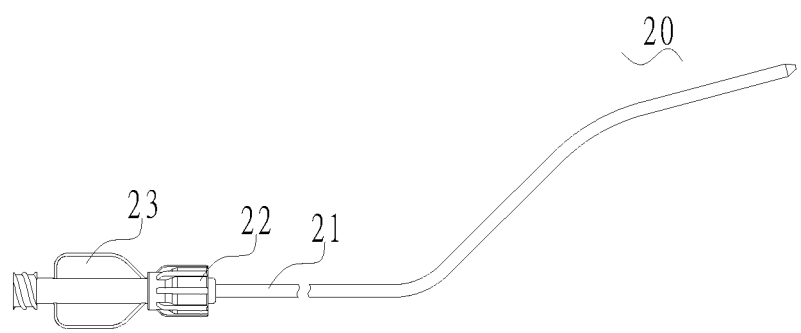
FIG. 2 is a schematic diagram of an expansion apparatus of the delivery system in FIG. 1.

With reference to FIG. 1 and FIG. 2, the delivery system 100 includes a delivery apparatus 10, an expansion apparatus 20, a loading apparatus 30, a pushing apparatus 40 and a hemostasis apparatus 50.

Figure 3:
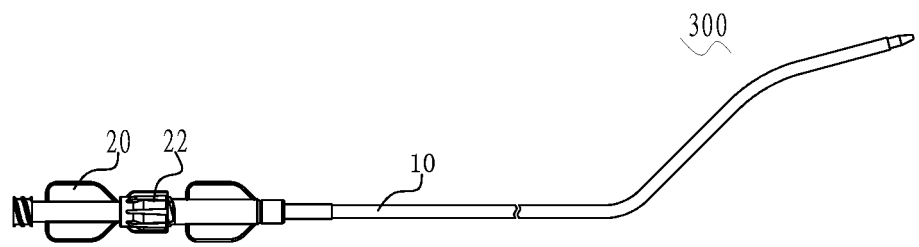
FIG. 3 is a schematic diagram of an expansion assembly consisting of a delivery apparatus and the expansion apparatus of the delivery system in FIG. 1.

With reference to FIG. 3 together, the distal end of the expansion apparatus 20 penetrates through the distal end of the delivery apparatus 10 to form an expansion assembly 300.

The distal end of the expansion assembly 300 passes through the atrial septum from a femoral vein along a rail built by a guide wire (not shown in the figure), and reaches the left atrial appendage; and then the expansion apparatus 20 is removed, but the delivery apparatus 10 remains in the body, thus building a channel from outside to inside of the body With reference to FIG. 1 again, after the channel from outside to inside of the body is built, the loading apparatus 30 is first connected between the hemostasis apparatus 50 and the delivery apparatus 10, and then the distal end of the pushing apparatus 40 penetrates through the hemostasis apparatus 50, the loading apparatus 30 and the delivery apparatus 10 in sequence, and then is detachably connected with the interventional medical device 200.

In this embodiment, the interventional medical device 200 is in threaded connection with the distal end of the pushing apparatus 40. It can be understood that the interventional medical device 200 also may be connected with the pushing apparatus 40 in other detachable ways, such as clamping connection, magnetic connection and pulling wire connection.

It should be noted that in some cases, the delivery system 100 may not include the loading apparatus 30; and the proximal end of a delivery sheath 11 is directly connected with the distal end of the hemostasis apparatus 50, and an inner cavity of the delivery sheath 11 is communicated with an inner cavity of the hemostasis apparatus 50.

Figure 4:
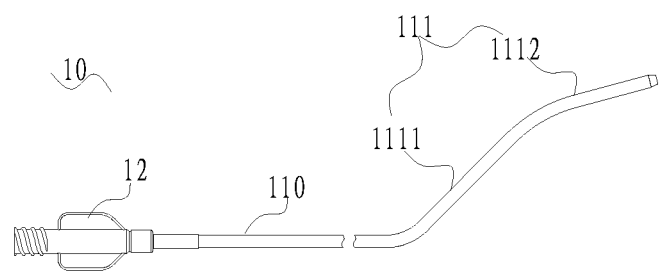
FIG. 4 is a schematic diagram of a delivery apparatus of the delivery system in FIG. 1.

With reference to FIG. 4 together, the delivery apparatus 10 includes the hollow delivery sheath 11 and a sheath connector 12 connected to the proximal end of the delivery sheath 11. The proximal end of the delivery sheath 11 is connected with the distal end of the loading apparatus 30, and the inner cavity of the delivery sheath 11 is communicated with an inner cavity of the loading apparatus 30.

The delivery sheath 11 includes a main body portion 110 and a shaping portion 111. The main body portion 110 is connected between the hemostasis apparatus 50 and the shaping portion 111. The shaping portion 111 includes a first shaping section 1111; an included angle between the extending direction of the first shaping section 1111 and the extending direction of the main body portion 110 ranges from 40 to 50 degrees; the extending direction of the first shaping section 1111 is a direction from the proximal end of the first shaping section 1111 to the distal end of the first shaping section 1111; and the extending direction of the main body portion 110 is a direction from the proximal end of the main body portion 110 to the distal end of the main body portion 110.

The shaping portion 111 also includes a second shaping section 1112. The first shaping section 1111 is connected between the main body portion 110 and the second shaping section 1112; an included angle between the extending direction of the second shaping section 1112 and a plane where the first shaping section 1111 and the main body portion 110 are located ranges from 30 to 40 degrees; and the extending direction of the second shaping section 1112 is a direction from the proximal end of the second shaping section 1112 to the distal end of the second shaping section 1112. Therefore, the shaping portion 111 is favorable for adapting to an anatomical structure of the left atrial appendage.

It can be understood that during clinical use, the second shaping section 1112 also may be omitted according to an actual requirement as long as the shaping portion 111 having the first shaping section 1111 may conform to anatomical structures of different individuals and different predetermined interventional treatment positions. The sheath wall of the delivery sheath 11 is of a multilayer structure, and includes a polytetrafluoroethylene material layer, a stainless steel woven layer and a polyether block amide layer from inside to outside in sequence.

With reference to FIG. 2 again, the expansion apparatus 20 includes an expansion tube 21, a first connection screw cap 22 which is located at the proximal end of the expansion tube 21 and is connected with the proximal end of the expansion tube 21, and an expansion tube connector 23 located at the proximal end of the first connection screw cap 22. The expansion tube 21 may be arranged in the delivery sheath 11 in a penetrating manner, and is used for assisting the delivery sheath 11 along the guide wire in building a vascular path; and the expansion tube 21 is made of polyethylene. The outer diameter of the expansion tube 21 is slightly less than the inner diameter of the delivery sheath 11, so that the distal end of the expansion tube 21 may enter the delivery sheath 11 from the proximal end of the delivery sheath 11, and penetrates through the delivery sheath 11 from the distal end of the delivery sheath 11. The expansion tube 21 has a shaping portion which is the same as the shaping portion 111 of the delivery sheath 11 in shape. The outer diameter of the head of the distal end of the expansion tube 21 is gradually increased from the distal end to the proximal end.

The first connection screw cap 22 may be in threaded connection with the proximal end of the delivery apparatus 10 to connect the delivery apparatus 10 with the expansion apparatus 20 to form the expansion assembly 300. The expansion tube connector 23 is used for limiting the proximal end of the expansion tube 21 to enter the delivery sheath 11.

Figure 5:
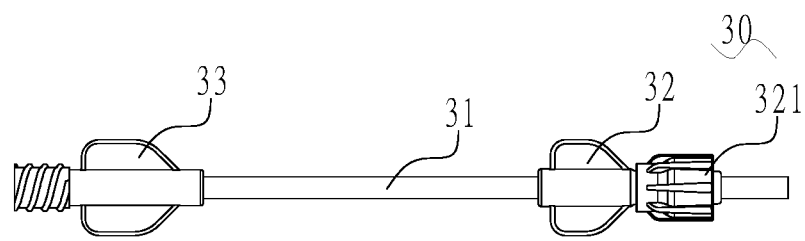
FIG. 5 is a schematic diagram of a loading apparatus of the delivery system in FIG. 1.

With reference to FIG. 1 and FIG. 5 together, after the channel from outside to inside of the body is built, the loading apparatus 30 is connected between the delivery apparatus 10 and the hemostasis apparatus 50. The loading apparatus 30 includes a hollow loader 31. The proximal end of the loader 31 is connected with the distal end of the hemostasis apparatus 50, and the distal end of the loader 31 is connected with the proximal end of the delivery sheath 11 of the delivery apparatus 10. An inner cavity of the loader 31 may be communicated with the inner cavity of the hemostasis apparatus 50.

The loading apparatus 30 also may include a loader front connector 32 connected to the distal end of the loader 31 and a loader rear connector 33 connected to the proximal end of the loader 31. A second connection screw cap 321 connected with the sheath connector 12 is arranged at the proximal end of the loader front connector 32. The loader rear connector 33 is connected with the hemostasis apparatus 50. The loader 31 is made of polyethylene.

Figure 6A:
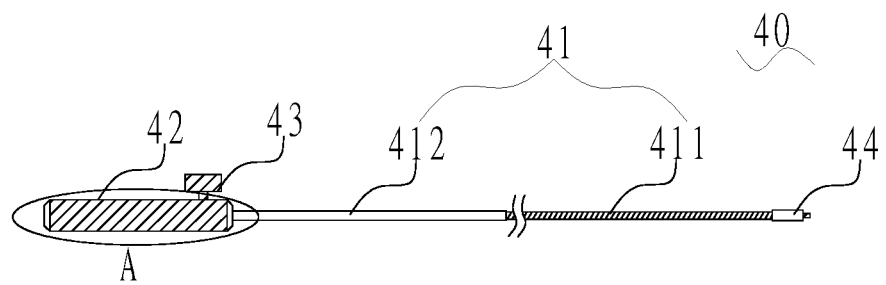
FIG. 6a is a schematic diagram and a local section view of a pushing apparatus of the delivery system in FIG. 1, wherein the pushing apparatus includes a steel cable, and the steel cable includes a long-strip type steel cable main body and an overlap film arranged on the outer surface of the steel cable main body.

With reference to FIG. 6a, the pushing apparatus 40 is used for pushing the interventional medical device 200, and in this embodiment, it is used for pushing the left atrial appendage occluder. The pushing apparatus 40 includes a steel cable 41. The steel cable 41 includes a long-strip type steel cable main body 411 and an overlay film 412 arranged on the outer surface of the steel cable main body 411; the steel cable main body 411 has a proximal end and a distal end which are opposite to each other; and the proximal end of the overlay film 412 is adjacent to the proximal end of the steel cable main body 411. The overlay film 412 is made of a thermoplastic elastomer.

In this embodiment, the overlay film 412 is made of a block polyether amide elastomer. The length of the overlay film 412 along the longitudinal central axis of the steel cable main body 411 is equal to or less than half of the length of the steel cable main body 411. To be specific, the length of the steel cable main body 411 ranges from 1,000 to 1,400 mm, and the length of the overlay film 412 ranges from 400 to 750 mm. In this embodiment, the length of the steel cable main body is 1,300 mm, and the length of the overlay film 412 is 600 mm. A distance between the distal end of the overlay film 412 and the distal end of the steel cable main body 411 is 700 mm.

It should be understood that the overlay film 412 also may be arranged at any required position between the proximal end and the distal end of the steel cable main body 411 as long as its supporting property for the steel cable main body 411 may meet an actual requirement. For example, the overlay film 412 is arranged on the outer surface of the middle section of the steel cable main body 411, that is, no overlay film is arranged on the outer surface, which is close to the proximal end, of the steel cable main body 411.

Figure 7:
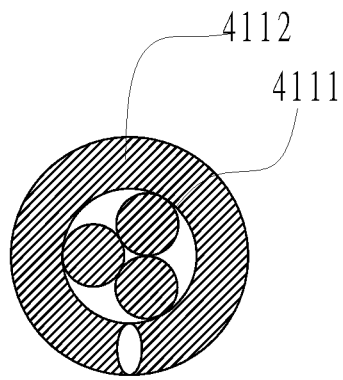

With reference to FIG. 7, the steel cable main body 411 includes a long-strip type inner core 4111 which is formed by twisting at least three strands of steel wires. In this embodiment, the inner core 4111 is formed by twisting three strands of steel wires; and the steel cable main body 411 also includes a steel wire 4112 arranged on the inner core 4111.

Figure 8:
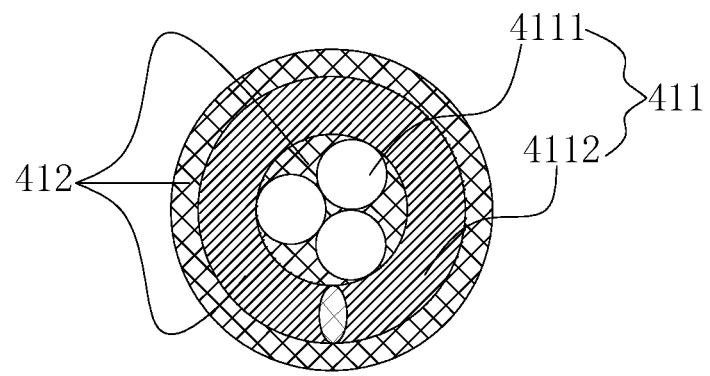

With reference to FIG. 8, the overlay film 412 is arranged on the outer surfaces of the inner core 4111 and the steel wire 4112. The steel cable 41 with the overlay film 412 may ensure that the distal end flexibly adapts to a bent blood vessel path, and is higher in supporting property and pushing property; and during delivery of the interventional medical device 200, it is difficult for the interventional medical device 200 to deviate from a predetermined position, thus shortening the operation time, and reducing the operation risk of patients.

It should be understood that the steel cable main body 411 also may only include a long-strip type inner core 4111 formed by twisting three strands of steel wires, and does not include the steel wire 4112 arranged on the inner core, so that the overlay film 412 is arranged on the outer surface of the inner core 4111.

With reference to FIG. 6a again, the pushing apparatus 40 also includes a steel cable handle 42 connected with the proximal end of the steel cable main body 411, a steel cable fastening screw 43 which is used for connecting the steel cable main body 411 with the steel cable handle 42, and a bolt 44 which is welded at the distal end of the steel cable main body 411 and is detachably connected with the interventional medical device 200.

Figure 6B:
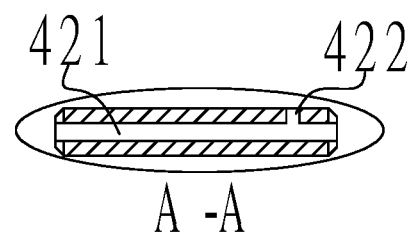

With reference to FIG. 6b, a steel cable containing cavity 421 is formed in the axial direction of the steel cable handle 42. The steel cable containing cavity 421 is used for containing the proximal end of the steel cable main body 411; a radial threaded side hole 422 is formed in the distal end of the steel cable handle 42; and the threaded side hole 422 is communicated with the steel cable containing cavity 421.

With reference to FIG. 6a and FIG. 6b at the same time, the steel cable fastening screw 43 is screwed into the threaded side hole 422, and its head end presses against the proximal end of the steel cable main body 411, so that the aim of fixing the steel cable main body 411 and the steel cable handle 42 may be fulfilled.

Figure 9A:
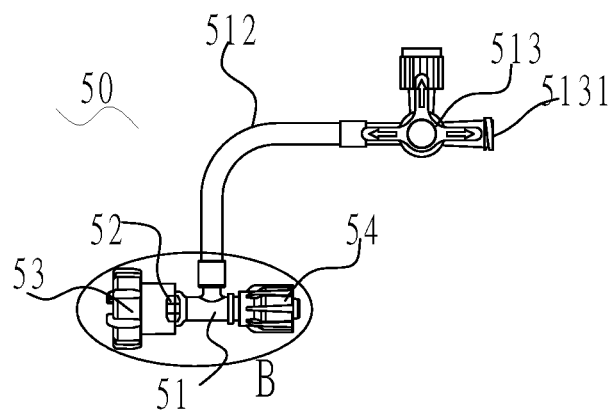
Figure 9B:
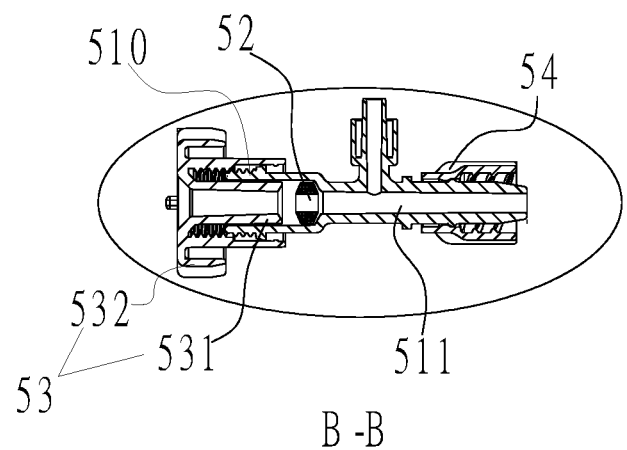

With reference to FIG. 9a and FIG. 9b at the same time, the hemostasis apparatus 50 includes a hemostasis valve body 51 having an inner cavity 511 and a sealing member 52 arranged in the inner cavity 511. A pore is formed in the sealing member 52. After the distal end of the steel cable main body 411 penetrates through the hemostasis valve body 51 from the distal end of the hemostasis valve body 51 via the pore, the distal end of the overlay film 412 of the steel cable 41 may penetrate through the distal end of the sealing member 52, and the overlay film 412 of the steel cable 41 cooperates with the sealing member 52 to isolate the distal end of the inner cavity 511 from the outside world.

The hemostasis valve body 51 may be in a T shape or Y shape. In this embodiment, the hemostasis valve body 51 is a T-shaped valve. An external thread 510 is formed on the outer surface, which is close to the proximal end of the hemostasis valve body 51, of the hemostasis valve body 51.

The hemostasis apparatus 50 also includes a pressing member 53 located at the proximal end of the hemostasis valve body 51 and a third connection screw cap 54 located at the distal end of the hemostasis valve body 51.

Figure 9C:
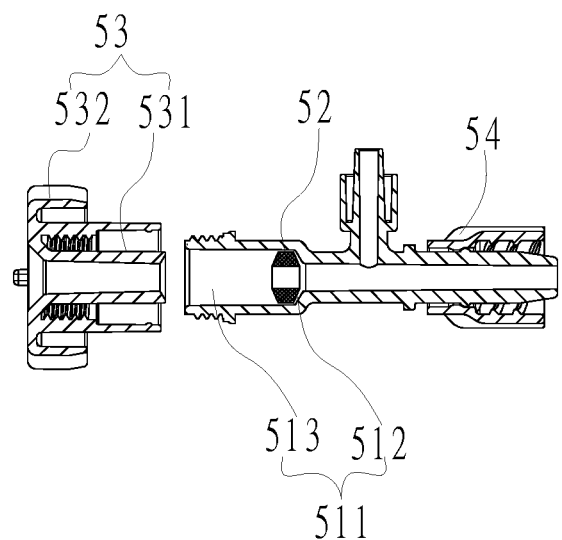

With reference to FIG. 9c, the inner cavity 511 has a columnar section 513 and a conical section 512 which are connected with each other; the columnar section 513 is closer to the proximal end of the hemostasis valve body 51 than the conical section 512; the diameter of the columnar section 513 is equal to that of the proximal end of the conical section 512; the diameter of the proximal end of the conical section 512 is greater than that of the distal end of the conical section 512; and the sealing member 52 is adjacent to the proximal end of the conical section 512. In this embodiment, the sealing member 52 is an O-shaped silica gel ring.

It can be understood that the conical section 512 may be arranged at any position of the inner cavity 511 as long as the distal end of the overlay film 412 of the steel cable 41 penetrates through the distal end of the sealing member 52 after the distal end of the steel cable main body 411 penetrates through the hemostasis valve body 51 from the distal end of the hemostasis valve body 51, and the overlay film 412 of the steel cable 41 may cooperate with the sealing member 52 to isolate the distal end of the inner cavity 511 of the hemostasis valve body 51 from the outside world.

The pressing member 53 includes a hollow pressing column 531 and a pressing screw cap 532 which surrounds the pressing column 531 and is connected with the pressing column 531; a containing space for containing the hemostasis valve body 51 is formed between the outer wall of the pressing column 531 and an internal thread of the pressing screw cap 532, and the distal end of the pressing column 531 is closer to the distal end of the hemostasis valve body 51 than the distal end of the thread of the pressing screw cap 532. The outer diameter of the pressing column 531 is less than the diameter of the columnar section 513 of the hemostasis valve body 51, so that the pressing column 531 may enter the inner cavity 511 of the hemostasis valve body 51; and after the hemostasis valve body 51 is in threaded connection with the pressing screw cap 532, the pressing column 531 may press against the sealing member 52.

Figure 9D:
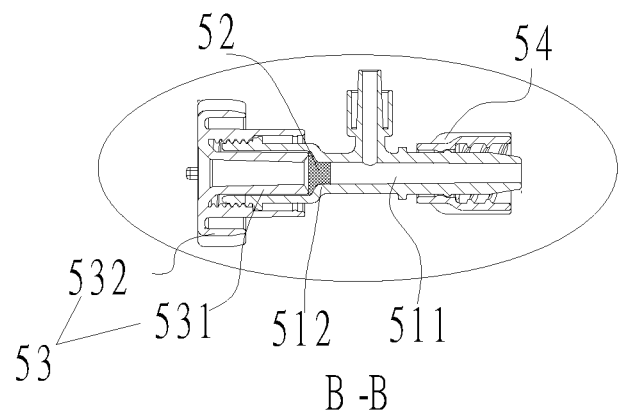
Figure 10:
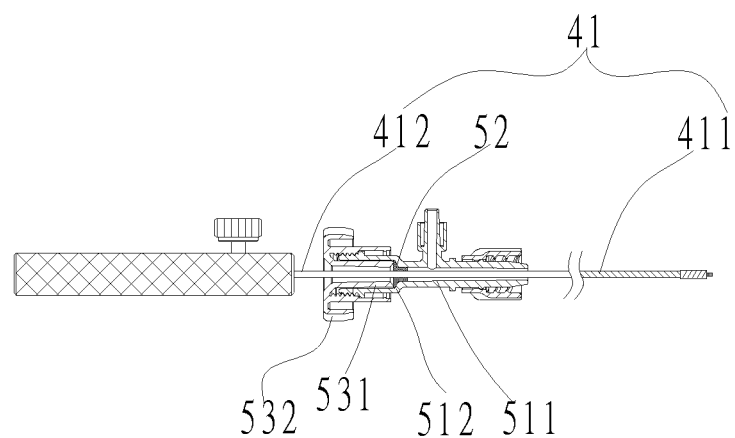
FIG. 10 is a schematic diagram of cooperation of the sealing member of the hemostasis apparatus in FIG. 9 and the overlay film of the pushing apparatus in FIG. 6.

With reference to FIG. 9d, when the pressing screw cap 532 is rotated clockwise, the pressing column 531 moves towards the distal end of the hemostasis valve body 51, and the sealing member 52 is pressed to move to the distal end of the conical section 512; and as the diameter of the proximal end of the conical section 512 is greater than that of the distal end, the portion, which enters the distal end of the conical section 512, of the sealing member 52 would generate an elastic deformation. With reference to FIG. 10, the sealing member 52 entering the distal end of the conical section 512 generates elastic deformation shrinkage, and then holds the overlay film 412 tight so as to isolate the distal end of the inner cavity 511 from the outside world.

With reference to FIG. 9b again, when the pressing screw cap 532 is rotated anticlockwise, the pressing column 531 moves towards the proximal end of the hemostasis valve body 51, and may not press against the sealing member 52, and the sealing member 52 moves towards the proximal end of the conical section 512, returns to a loose state, and is not in tight contact with the overlay film 412, so that the distal end of the inner cavity 511 is not isolated from the outside world.

It can be understood that the sealing member 52 also may be fixed in the hemostasis valve body 51 as long as the sealing member 52 may hold the overlay film 412 tight at the moment, for example, a circular hole of the sealing member 52 is small relative to the outer diameter of the overlay film 412, or the sealing member 52 is a sealing sheet with a crossed incision, and the like.

With reference to FIG. 9a again, a connection hose 512 communicated with the inner cavity 511 is also arranged on the side surface of the hemostasis valve body 51; the end portion, which is connected with the hemostasis valve body 51, of the connection hose 512 is closer to the distal end of the hemostasis valve body 51 than the sealing member 52; the other end of the hose 512 is connected with a three-way valve 513; a 6% Ruhr cone connection port 5131 of the three-way valve 513 is connected with an external infusion device; when the distal end of the inner cavity 511 is isolated from the outside world, the three-way valve 513 may be connected with an external radiography device; and before the interventional medical device 200 is released, an occluding effect is assessed by means of radiography.

Embodiment II

This embodiment is a manufacturing method of the steel cable 41 of Embodiment I.

Figure 11:
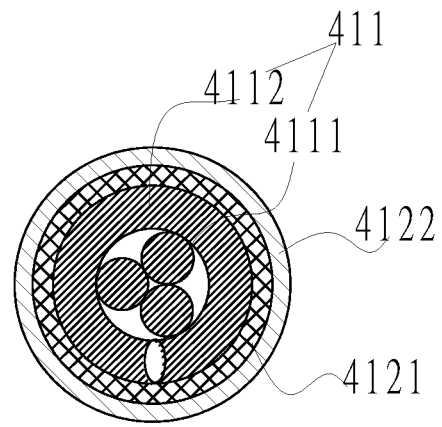
FIG. 11 is a sectional view of a steel cable main body covered by multiple layers of tubular bodies of a second embodiment of the utility model.
Figure 12:
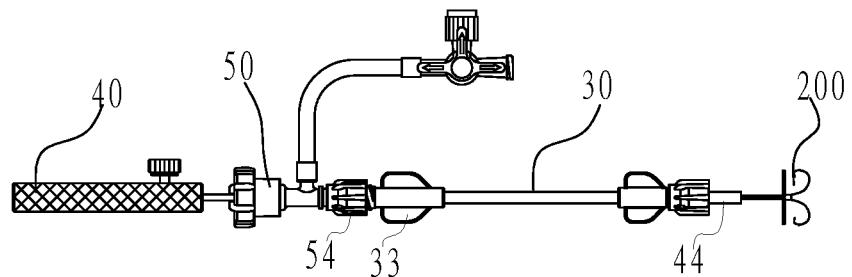
FIG. 12 is a schematic diagram of a third embodiment of the utility model after a hemostasis apparatus, a loading apparatus, a pushing apparatus and an interventional medical device are assembled.

The method includes:

(1) with reference to FIG. 11, a polyether block amide (French Arkema, trade name: Pebax) tubular body 4121 with the wall thickness of 0.2 mm sleeves the outer surface of a steel cable main body 411, and the proximal end of the polyether block amide tubular body 4121 is adjacent to the proximal end of the steel cable main body 411; a fluorinated ethylene-propylene copolymer (FEP) heat shrink tubing 4122 with the wall thickness of 0.3 mm sleeves the polyether block amide tubular body 4121, thus obtaining a multilayer tubular body-covered steel cable main body 411.

The inner diameter of the heat shrink tubing 4122 before shrinkage is slightly greater than the outer diameter of the tubular body 4121, and the melting point of the tubular body 4121 is lower than that of the heat shrink tubing 4122.

In this embodiment, the melting point of the tubular body 4121 is 159° C., and for the heat shrink tubing 4122, its heat shrinkage temperature is 210° C., and its melting point is about 320° C.

(2) The tubular body 4121 is melted within a temperature range of 180° C. to 220° C. to integrate the tubular body 4121 with the steel cable main body. To be more specific, in this embodiment, the multilayer tubular body-covered steel cable main body 411 is heated to 210° C.; at the moment, the polyether block amide tubular body 4121 is melted and covers the outer surface, which is adjacent to the proximal end of the steel cable main body 411, of the steel cable main body 411 so as to be integrated with the steel cable main body 411, and the FEP heat shrink tubing 4122 on the outer layer would shrink, but may not be melted.

(3) The heat shrink tubing 4122 on the outer layer is removed to obtain the steel cable 41.

The structure of the steel cable 41 is as shown in FIG. 8, and the steel cable 41 includes the steel cable main body 411 and an overlay film 412; polyether block amide covers the outer surface of a long-strip type inner core 4111 and the outer surface of a steel wire 4112 arranged on the inner core 4111, thus forming the overlay film 412.

It can be understood that the tubular body 4121 also may be made of a thermoplastic polyurethane elastomer or other thermoplastic elastomers as long as the heat shrink tubing having the melting point higher than that of the thermoplastic elastomer sleeves it.

The structure obtained by the manufacturing method guarantees the flexibility of the distal end of the steel cable main body 411, and also improves the supporting property of the proximal end of the steel cable main body 411, thus improving the usability of a delivery system, and facilitating pushing of an interventional medical device in a human body environment.

It can be understood that ways of applying the overlay film 412 to the steel cable main body 411 also may include thermal spraying, dispensing, electroplating, vacuum coating, evaporation coating, sputtering, chemical vapor deposition and the like. The material of the overlay film 412 also may include a macromolecular material such as a thermoset elastomer, a metal material or a polymer as long as the supporting property of the steel cable main body 411 having the overlay film 412 meets an actual requirement.

Embodiment III

Figure 13:
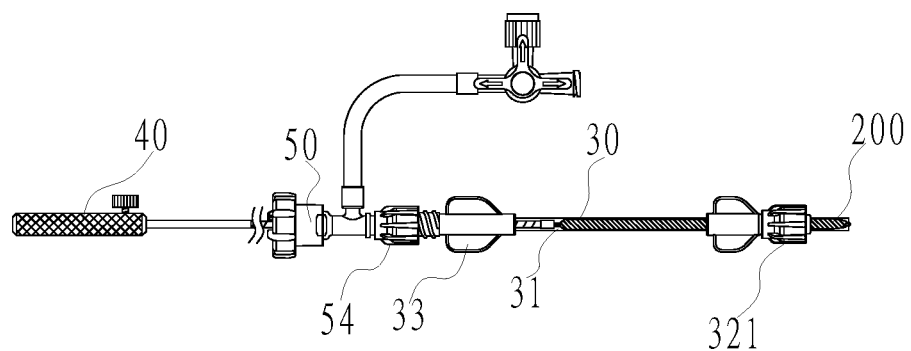
FIG. 13 is a schematic diagram of the loading apparatus as shown in FIG. 12 after the interventional medical device is put into the loading apparatus.

This embodiment is a method of applying the delivery system 100 of Embodiment I to clinical delivery of an interventional medical device 200, including:

(1) the distal end of an expansion apparatus 20 penetrates through the distal end of a delivery apparatus 10, and is in threaded connection with the proximal end of the delivery apparatus 10 through a first connection screw cap 22 of the expansion apparatus 20, thus forming an expansion assembly 300 as shown in FIG. 3; the expansion assembly 300 passes through the atrial septum from a femoral vein along a rail built by a guide wire (not shown in the figure), and reaches the left atrial appendage; then the expansion apparatus 20 is removed, but the delivery apparatus 10 remains in the body, thus building a channel from outside to inside of the body;

(2) a third connection screw cap 54 at the distal end of a hemostasis apparatus 50 is connected with a loader rear connector 33 of a loading apparatus 30, and the distal end of a pushing apparatus 40 penetrates through the hemostasis apparatus 50 and the loading apparatus 30 in sequence, and then is in threaded connection with the interventional medical device 200 through a bolt 44 located at the distal end of the pushing apparatus 40, thus obtaining the hemostasis apparatus 50, the loading apparatus 30 and the pushing apparatus 40 which are assembled; then the pushing apparatus 40 is retracted to the proximal end to collect the interventional medical device 200 into an inner cavity of a loader 31, thus obtaining the loading apparatus 30 loaded with the interventional medical device 200 as shown in FIG. 13;

(3) the loading apparatus 30 which is loaded with the interventional medical device 200 as shown in FIG. 13 and is obtained in the step (2) is connected with a sheath connector 12, thus obtaining the delivery system 100 with the interventional medical device 200 as shown in FIG. 1;

(4) a pressing screw cap 532 is rotated anticlockwise to enable a sealing member 52 to be in a natural loose state, and the pushing apparatus 40 is pushed to the proximal end of the delivery system 100 so as to deliver the interventional medical device 200 to a predetermined position in the left atrial appendage and spread it;

(5) the pressing screw cap 532 is rotated clockwise; at the moment, the sealing member 52 in an inner cavity 511 of a hemostasis valve body 51 is pressed by a pressing column 531 to move to the distal end of the conical section 512, and hold an overlay film 412 tight, so that the distal end of the inner cavity 511 is isolated from the outside world; a three-way valve 513 in the hemostasis apparatus 50 is opened to connect a manual pushing injection apparatus (not shown in the figure) filled with a radiocontrast agent to a 6% Ruhr cone connector 5131 of the three-way valve 513;

(6) the manual pushing injection apparatus is pushed to push the radiocontrast agent to the distal end of an inner cavity of the hemostasis valve body 51 in a state of being isolated from the outside world; as a steel cable main body 411 is not separated from the spread interventional medical device 200 at the moment, whether the spread position of the interventional medical device 200 is the optimal or not and whether an operation effect is satisfactory or not may be observed through imaging equipment;

(7) if the operation effect is poor, and it needs to adjust the spread position of the interventional medical device 200, the pressing screw cap 532 is rotated anticlockwise at first to enable the sealing member 52 to return to the loose state, and the steel cable main body 411 is retracted to drive the interventional medical device 200 to be retracted into a delivery sheath 11; then a sheath connector 12 is adjusted to adjust the distal end of the delivery sheath 11 to a better position;

(8) the interventional medical device 200 is pushed to the better position and then is spread; the pressing screw cap 532 is rotated clockwise to enable the distal end of the inner cavity 511 to be isolated from the outside world, and radiography assessment is carried out again; and after the operation effect is assessed to be satisfactory, the threaded connection between the bolt 44 at the distal end of the steel cable main body 411 and the interventional medical device 200 is relieved, thus releasing the interventional medical device 200, and other components are removed to complete the operation.

Embodiment IV

After the steps (1) to (6) of Embodiment III are carried out, during radiography assessment, if the model of the interventional medical device is inappropriate and needs to be changed, and the operation effect is dissatisfactory, the pressing screw cap 532 is rotated anticlockwise at first to enable the sealing member 52 to return to the loose state; second, a steel cable 41 is retracted to the proximal end of a delivery system 100 to drive the interventional medical device to be collected into a delivery sheath 11; third, the connection between a second connection screw cap 321 of a loading apparatus 30 and a sheath connector 12 is cut off; then the inappropriate interventional medical device is removed from the sheath 11, the threaded connection between the inappropriate interventional medical device and the steel cable 41 is cut off, and a new interventional medical device is replaced; fifth, steps (3) to (7) of Embodiment III are repeatedly executed until the appropriate interventional medical device is pushed to an appointed treatment position; and finally, the step (8) is executed to complete the operation.

Therefore, the delivery system may effectively assist a doctor in finishing an assessment of the operation effect during operation, and the radiography assessment may be carried out without releasing the device, so that the operation process is more convenient and faster.

By covering the outer surface of the steel cable main body of the steel cable with a thermoplastic overlay film, the disclosure improves the supporting properties of the steel cable, and facilitates pushing of the interventional medical device.

As a twisted structure inside a common pushing steel cable has a gap, the occluding effect may not be judged through radiography before the pushing steel cable is separated from the interventional medical device, but is only judged through ultrasonic observation, so that resources equipped for operation are added. When a treatment site with a complicated anatomical structure, such as the left atrial appendage, is operated on, ultrasonic observation is not as clear as radiography observation, thus reducing the treatment effect of the operation. If the size of the interventional medical device is selected inappropriately, and the spread position is not good, the interventional medical device only has to be recycled at first, and then is delivered and released, thus judging the operation effect. In this delivery system of the device, the sealing member cooperating with the overlay film of the steel cable is arranged in the hemostasis valve body so that the distal end of the inner cavity of the hemostasis valve body may be isolated from the outside world during operation, real-time radiography assessment may be carried out during the operation, controllability of releasing the device and operation effect assessment are realized, and the harm to patients, which is caused by recycling of the interventional medical after being released, due to an inappropriate model selection of the interventional medical device or requirement for adjustment of the spread position, is effectively avoided.

The above-mentioned embodiments are merely preferred embodiments, and are not intended to limit the present application. Any modifications, equivalent replacements, improvements and the like that are made without departing from the spirit and the principle of the disclosure shall all fall within the scope of protection of the present application.

The invention claimed is:

1. A pushing apparatus, comprising:
a steel cable which comprises a long-strip type steel cable main body comprising an inner core formed by at least three twisted strands of wire, a steel wire arranged on the inner core, and an overlay film arranged on an outer surface of the steel wire of the long-strip type steel cable main body, wherein the overlay film is further arranged on an outer surfaces of the inner core and the steel wire or on the outer surface of the inner core.

2. The pushing apparatus according to claim 1, wherein the long-strip type steel cable main body has a proximal end and a distal end which are opposite to each other; and a proximal end of the overlay film is adjacent to the proximal end of the long-strip type steel cable main body.

3. The pushing apparatus according to claim 1, wherein the overlay film is made of a thermoplastic elastomer.

4. The pushing apparatus according to claim 3, wherein the thermoplastic elastomer comprises polyether block amide or thermoplastic polyurethane.

5. The pushing apparatus according to claim 1, wherein a length of the overlay film arranged on the steel wire along the longitudinal central axis of the long-strip type steel cable main body is equal to or less than half of the length of the steel cable main body.

6. A delivery system, comprising the pushing apparatus according to claim 1.

7. The delivery system according to claim 6, further comprising a hemostasis apparatus; the hemostasis apparatus comprises a hemostasis valve body having an inner cavity and a sealing member arranged in the inner cavity of the hemostasis valve body; a pore is formed in the sealing member; after the distal end of the steel cable main body penetrates through the hemostasis valve body from the distal end of the hemostasis valve body via the pore, the overlay film of the steel cable cooperates with the sealing member to isolate the distal end of the inner cavity of the hemostasis valve body from the outside world.

8. The delivery system according to claim 7, further comprising a delivery sheath; the proximal end of the delivery sheath is connected with the distal end of the hemostasis apparatus, and an inner cavity of the delivery sheath is communicated with the inner cavity of the hemostasis apparatus.

9. The delivery system according to claim 8, wherein the delivery sheath comprises a main body portion and a shaping portion; the main body portion is connected between the hemostasis apparatus and the shaping portion; the shaping portion comprises a first shaping section; an included angle between the extending direction of the first shaping section and the extending direction of the main body portion ranges from 40 to 50 degrees; the extending direction of the first shaping section is a direction from the proximal end of the first shaping section to the distal end of the first shaping section; and the extending direction of the main body portion is a direction from the proximal end of the main body portion to the distal end of the main body portion.

10. The delivery system according to claim 9, wherein the shaping portion further comprises a second shaping section; the first shaping section is connected between the main body portion and the second shaping section; an included angle between the extending direction of the second shaping section and a plane where the first shaping section and the main body portion are located ranges from 30 to 40 degrees; and the extending direction of the second shaping section is a direction from the proximal end of the second shaping section to the distal end of the second shaping section.

11. The delivery system according to claim 9, wherein the delivery system further comprises an expansion tube; the outer diameter of the expansion tube is slightly less than the inner diameter of the delivery sheath; and the outer diameter of the head of the distal end of the expansion tube is gradually increased from the distal end to the proximal end.

12. The delivery system according to claim 11, wherein the expansion tube is provided with a shaping portion which is the same as the shaping portion of the delivery sheath in shape.

13. The delivery system according to claim 8, wherein the delivery system further comprises a hollow loader connected between the delivery sheath and the hemostasis apparatus; and an inner cavity of the loader is communicated with the inner cavities of the delivery sheath and the hemostasis apparatus.

14. The delivery system according to claim 7, wherein the inner cavity of the hemostasis valve body has a conical section; the diameter of the proximal end of the conical section is greater than that of the distal end of the conical section; and the sealing member is adjacent to the proximal end of the conical section.

15. The delivery system according to claim 7, wherein the delivery system is used for delivering a left atrial appendage occluder; and the steel cable is detachably connected with the left atrial appendage occluder.

* * * * *